United States Patent [19]
Rose

[11] Patent Number: 5,423,681
[45] Date of Patent: Jun. 13, 1995

[54] INTRAORAL METHOD AND CHEWING COMPOUND FOR PROVIDING PROPER OCCLUSION

[76] Inventor: James L. Rose, 3400 Milam La., Lexington, Ky. 40502

[21] Appl. No.: 300,662

[22] Filed: Sep. 2, 1994

Related U.S. Application Data

[63] Continuation of Ser. No. 195,590, Feb. 9, 1994, abandoned, which is a continuation of Ser. No. 922,246, Jul. 31, 1992, abandoned.

[51] Int. Cl.⁶ ................................................. A61C 5/00
[52] U.S. Cl. ..................................... 433/215; 433/166
[58] Field of Search ................. 433/215, 216, 229, 166

[56] References Cited

U.S. PATENT DOCUMENTS

| | | | |
|---|---|---|---|
| 1,592,013 | 7/1926 | Taylor | 433/125 |
| 2,929,143 | 3/1960 | Roubian | 433/167 |
| 3,590,120 | 6/1971 | Muhler | 424/48 |
| 3,686,761 | 8/1972 | Gravon | 433/71 |
| 4,170,633 | 10/1979 | Wagenknecht et al. | 424/48 |
| 4,828,820 | 5/1989 | Glass et al. | 424/48 |

Primary Examiner—Cary E. O'Connor
Attorney, Agent, or Firm—King and Schickli

[57] ABSTRACT

A method of providing proper occlusion between natural teeth/natural teeth and a partial restoration/upper and lower plates of a full restoration includes the initial step of examining the occlusion and identifying high spots. Next a chewing compound is selected including an abrasive of a grade between 100 and 220 grit or a polish for providing controlled abrasive or polishing action. This step is then followed by the chewing of the compound for a period of three to fifteen minutes to remove the high spots, polish the teeth and provide overall better occlusion. The chewing compound utilized includes a bulk chewing material that is non-stick with respect to dental restorations and natural teeth. This material is covered and/or impregnated with a polish/abrasive powder material.

29 Claims, 1 Drawing Sheet

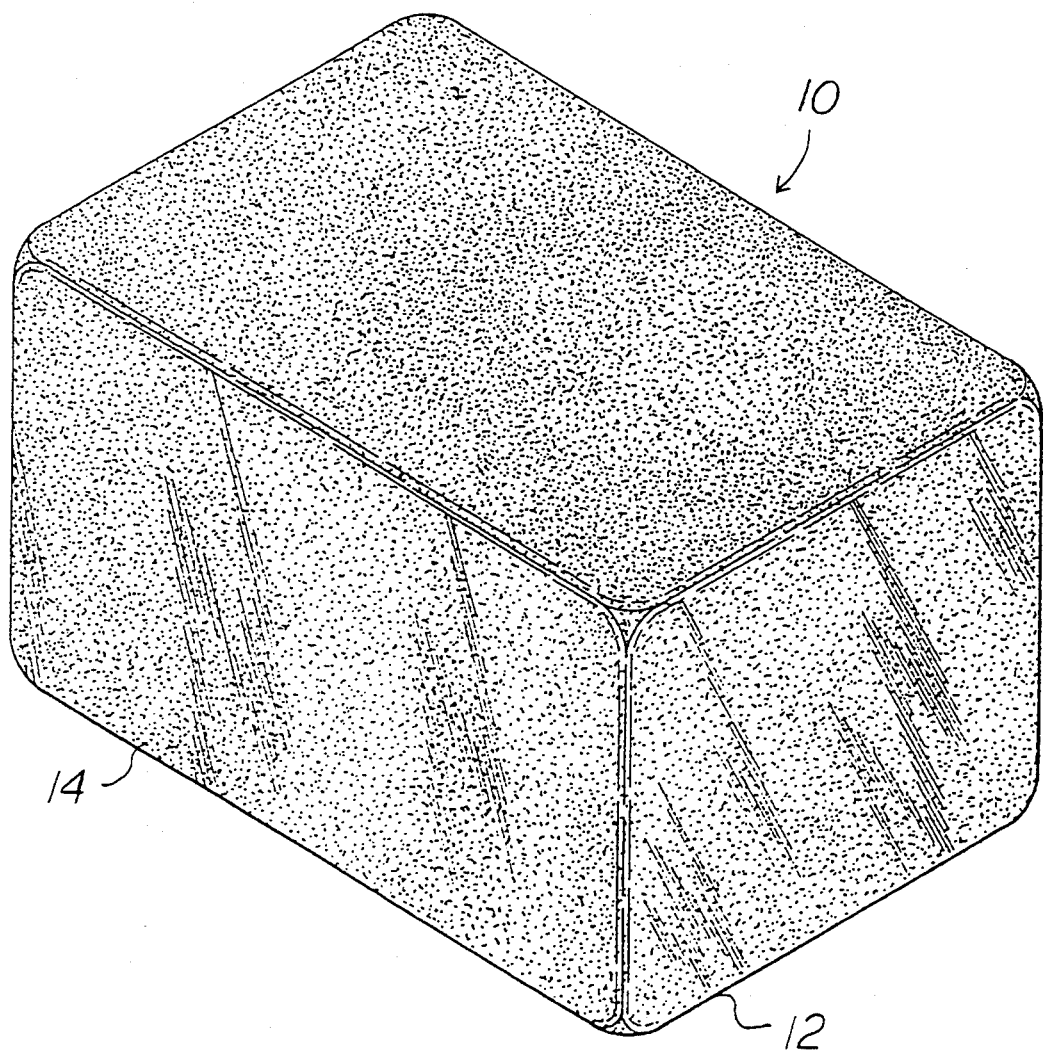

INTRAORAL METHOD AND CHEWING COMPOUND FOR PROVIDING PROPER OCCLUSION

This is a continuation of U.S. patent application Ser. No. 08/195,590 filed Feb. 9, 1994 which was a continuation of U.S. patent application Ser. No. 07/922,246 filed Jul. 31, 1992, both now abandoned.

TECHNICAL FIELD

The present invention relates generally to the dental field and, more particularly, to an intraoral method and chewing compound particularly adapted for providing proper occlusion between the natural teeth, partial dental restorations and the natural teeth and upper and lower plates of full dental restorations.

BACKGROUND OF THE INVENTION

Malocclusion or abnormality in the proper alignment and the coming together of teeth of the upper and lower jawbones is the most prevalent problem in dentistry today. Approximately 90% of individuals suffer from malocclusion in one form or another.

Malocclusion typically results from a "high spot" in the upper or lower teeth/restoration wherein contact is initially made. As the jaw is able to exert tremendous pressure during chewing, stresses are concentrated at this high spot. Due to this concentration of stress an unequalized pressure is placed upon the teeth and the jawbone. Over time the unequalized pressure may result in drifting of individual teeth, gum recision and even the destruction of periodontal bone. The temporal mandibular joint that controls the chewing function may also be subjected to uneven wear that can lead to a particularly painful condition. In severe cases the temporal mandibular joint may need to be replaced.

Although malocclusion has been recognized in dentistry as a significant problem, no particularly efficient treatment for the malady has been developed up to the present time. In fact, the problem has usually only been addressed within the context of positioning partial and complete dental restorations including, for example, bridges, inlays, crowns and full upper and lower plates. Very significant discomfort results from the concentration of stresses discussed above when such restorations are positioned without properly addressing and providing the desired occlusion. For example, plates may shift as a result of malocclusion and pinch the gum against the jaw bone during chewing. Such a painful condition must be avoided if the restoration procedure is to be effective and the patient satisfied.

Accordingly, dentists positioning bridges, inlays, crowns and upper and lower plates typically utilizes carbon paper or other means to identify high points where stresses are concentrated during chewing. More particularly, a piece of carbon paper is placed between the upper and lower teeth, whether natural or restored, and the patient then bites down in the normal chewing manner. The mouth is then opened and the carbon paper removed. Marks or traces are left by the carbon paper on the contact points between the teeth/restoration. These marks allow the identification of high points or areas of strong contact and low points or areas of no contact where the teeth are essentially not functioning to masticate food.

Once the high points are identified, the dentist may utilize a grinder to grind down the high points and bring them more in line with the other teeth. Unfortunately, this is an inexact procedure but it is the best that has been developed up until the present invention. Accordingly, a need has clearly been identified for an improved method of providing proper occlusion and balancing the bite of a patient.

SUMMARY OF THE INVENTION

Accordingly, a primary object of the present invention is to provide a safe, simple and inexpensive method for providing proper occlusion between the natural teeth, partial dental restorations and the natural teeth and upper and lower plates of full dental restorations.

Another object of the present invention is to provide an efficient and effective method for balancing the bite of a patient so as to restore full function of all the teeth/dental restoration and thereby evenly distribute the stresses of chewing over the upper and lower jaw bones. As described in greater detail elsewhere in this document, this even distribution of the stresses during chewing serves to significantly enhance the oral health of a patient.

Yet another object of the present invention is to provide a chewing compound including a bulk chewing material that holds the necessary abrasive to allow the removal of high spots between teeth/restorations resulting in malocclusion. Advantageously, the chewing compound functions in the natural environment of the mouth in conjunction with the natural chewing action of the patient to ensure that the grinding down of the high spots is occurring at the necessary points and to the necessary degree to provide proper occlusion.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a method of providing proper occlusion between natural teeth of the upper and lower jaw bones is provided. The method includes the step of examining the occlusion of the natural teeth and identifying any high spots. Next is the selecting of a chewing compound including an abrasive of a grade between 100 and 220 grit for providing controlled abrasive action on the natural teeth. This is followed by the chewing of the abrasive chewing compound for a period of 3-15 minutes to abrade the high spots and provide overall better occlusion.

More specifically, following this initial procedure the occlusion of the teeth may be reexamined. If warranted, the steps of selecting a chewing compound and chewing the chewing compound for a second period of time may then be completed. In the event the teeth have been sufficiently abraded to remove the high spots a chewing compound may be selected including a polish such as fine pumice sand. During chewing the pumice sand serves to smooth the abraded surfaces of the teeth.

In accordance with a further aspect of the present invention, where particularly prominent high spots are identified upon initial examination, it may be necessary to first grind down the high spots with a grinding tool in a manner known in the art prior to chewing the abrasive chewing compound. The appropriate procedure to be followed will be determined by the dental professional completing the examination and performing the procedure.

During chewing of the abrasive chewing compound, some abrasive may be released into the mouth of the patient. While the abrasive is non-toxic and not particularly harmful if swallowed, it is desired to expel the released abrasive. This is also true of any polish that might be released during the polishing step. Further, following the procedure it is desirable to rinse with an antiseptic. Additionally, in accordance with standard dental practice it is also desirable to subsequently provide the patient with a fluoride rinse to strengthen and protect the tooth enamel.

It should also be appreciated that over time certain dental procedures or events may effect occlusion. Accordingly, it is necessary to repeat the procedure as necessary, such as, for example, every 6-24 months, in order to maintain proper occlusion. More particularly, a loss of a tooth or the positioning of a crown or other restoration is the type of event that may adversely effect occlusion. The adverse effect may, however, be quickly, easily and efficiently countered utilizing the present method. Further, it should be appreciated that the procedure may be performed conveniently in a relatively short period of time during a typical visit to a dentist for examination.

In accordance with still another aspect of the present invention, the procedure outlined above may be followed to provide proper occlusion between a dental restoration and natural teeth or both upper and lower plates of a complete dental restoration. The steps as outlined above are equally relevant and applicable. The only significant difference may be found in the grade of abrasive utilized as dental restorations are construction from a harder material than teeth. Accordingly, a courser grade abrasive may be required to provide the desired abrading action.

In accordance with yet another aspect of the present invention, a chewing compound is provided for correcting malocclusion. This compound includes a bulk chewing material that is particularly designed and adapted to not stick to dental restorations and natural teeth. The non-stick feature is essential if the bulk chewing material is to function properly and allow the application of the desired abrasive action against the high spots that need to be ground away to provide proper occlusion.

A polish or abrasive powder material having a grade of between 100 and 220 grit is provided in or on the bulk chewing material. More particularly, the powder material may be sprinkled over the outer surface of the bulk chewing material when it is soft so as to stick thereto and/or impregnated within a chunk of the bulk chewing material.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. The drawing FIGURE is a perspective view of the abrasive chewing compound of the present invention. Reference will now be made in detail to the present preferred embodiment of the invention, an example of which is illustrated in the accompanying drawing.

DETAILED DESCRIPTION OF THE INVENTION

Reference is now made to the drawing FIGURE showing the chewing compound 10 of the present invention for correcting malocclusion and balancing the bite of a patient. The chewing compound includes a bulk chewing material 12 that is coated and/or impregnated with a polish or abrasive powder material 14. The polish or abrasive may, for example, be carborundum, graphite, pumice sand or any other abrasive used and approved by regulatory agencies for dental purposes. Preferably, a grade of abrasive between 100 and 220 grit is utilized. A finer grade of abrasive (e.g. 220 grit) is selected to correct malocclusion occurring to only a small degree and to grind high spots from relatively soft or natural teeth. In contrast, a relatively course grade (e.g. 100 grit) is selected in order to grind high spots from upper and lower plates of relatively hard dental restoration material such as porcelain. A polish is utilized after the abrasive to smooth any roughness created by the abrasive during the removal of the high spots.

In order to ensure proper function and the desired abrasive action during chewing, the bulk chewing material selected is of a type that does not stick to natural teeth and dental restorations. Of course, since the chewing compound does not stick and bind to teeth or restorations this messy and inconvenient problem is avoided. Further, no time is lost in removal/cleaning of the chewing material and abrasives from the teeth following treatment. Such a non-tacky abhesive bulk chewing material is, for example, available from Wm. Wrigley Jr. Company of Chicago, Ill. and sold under the trademark Freedent.

A method of providing proper occlusion between natural teeth of the upper and lower jawbones will now be described in detail. It is most important to complete this procedure on completing orthodontics, periodontia, crown and bridge operative dentistry and prosthodontia. It should be recognized, however, that it is also appropriate to complete this procedure regularly, such as during each visit to your dentist for cleaning and a checkup.

In accordance with the first step of the method or procedure, the natural teeth, the natural teeth and partial restoration or the upper and lower plates of a complete restoration are examined in order to identify high spots. This may be done in any way known in the art including but not limited to visual examination, the utilization of occlusal wax and the utilization of carbon paper. Advantageously, as is known, the occlusal wax and carbon paper leave visual markings indicating the points of contact between the teeth/restoration. By studying these marks, the high spots of the bite may be identified. If these high spots are abraded or buffed, they may be reduced or eliminated. Upon elimination of the high spots, substantially all of the teeth may be effectively brought into contact simultaneously and a balanced bite achieved.

Through the examination the dental professional is able to identify the extent and degree to which malocclusion exists for a particular patient. Taking into consideration the extent and/or prominence of the high spots and the architecture of the patient's mouth (e.g. natural teeth, partial restoration and natural teeth, full dental restoration), the dental professional then selects a chewing compound of the type described above including an abrasive of a grade between 100 and 220 grit. A relatively course grade (e.g. 100 grit) is selected to initially remove significant high spots from full dental restorations. In contrast, a medium grade (e.g. 120 grit) could be selected to remove prominent high spots from a patient having a partial restoration and natural teeth. In further contrast, a relatively fine abrasive (e.g. 220) may be selected when, for example, the patient has all natural teeth and only a slight case of malocclusion. Where a very prominent high spot exists, a grinder may be utilized in a manner known in the art to grind down the high spot to a less prominent level before utilizing the abrasive chewing material.

When utilizing coarse abrasive of, for example, 100 grit, between 4.0 and 5.0 grams of abrasive is provided for each 3.0 grams of bulk chewing material. When utilizing a relatively medium grade abrasive of, for example 120 grit, between 2.4 and 3.5 grams of abrasive is provided for each 3.0 grams of bulk chewing material. Finally, when utilizing a relatively fine grade of abrasive of, for example, 220 grit between 2.4 and 3.5 grams of abrasive is provided for each 3.0 grams of bulk chewing material.

Next, the patient is placed in an upright sitting position in order to bring the skeleton and musculature into geometrical alignment with the normal posture assumed by the patient during eating. Advantageously, this ensures that the normal eating motion of the jaw is assumed. This advantageously allows the proper occlusal planes to be preserved and brings the natural teeth/natural teeth and partial restoration/full restoration into position to mesh as well as possible.

More particularly, the method and procedure continues with the patient chewing the selected abrasive chewing compound for a period of from three to fifteen minutes, depending upon the coarseness or grade of the abrasive and the extent of the high spots to be removed, in order to abrade the high spots and provide overall better occlusion and meshing of the teeth/restoration. Typically a patient has a favorite place to chew and it has been found that this place usually corresponds to the existing high spots that need to be abraded. Accordingly, the patient naturally works the chewing gum to the place of need.

As the abrasive chewing compound is chewed, some of the abrasive is released. While the abrasive is non-toxic and will not harm the patient if swallowed in the small quantities that are utilized, it is desired to have the patient expel the abrasive from the mouth during the procedure.

Once chewing is completed, the abrasive chewing compound is expelled from the mouth. The patient may then rinse with water to remove any residual abrasive released from the compound. The patient may then be reexamined to confirm the further care necessary to balance the bite. If necessary, the step of chewing an abrasive chewing compound for a period of three to fifteen minutes may be repeated to further abrade the high spots. Alternatively, it may be desirable to remove any roughness caused to the surface of the teeth by the abrasive material in the abrasive chewing compound. Accordingly, the patient may be again positioned in an upright seating position. Subsequent to this the patient chews a polishing chewing compound incorporating a very fine pumice sand in a non-stick chewing material. The polishing chewing compound is chewed for a period of time of from three to fifteen minutes.

Once again, during chewing it should be appreciated that some polish may be released from the chewing compound. This polish should be expelled although, once again, swallowing of the polish does not represent a significant health hazard. Once chewing of the polishing chewing compound is completed, the polishing chewing compound is expelled and the patient is directed to rinse with water to remove any residual polish released from the compound.

If desired, an additional reexamination may then be performed visually or utilizing occlusal wax or carbon paper. It is then desirable to have the patient rinse with an antiseptic to kill any germs. Subsequent to this, the patient may be asked to rinse with a fluoride preparation to aid in strengthening the enamel coat on the natural teeth. Further, in order to ensure that the proper balance of the bite is maintained over time, the entire procedure including the examining, selecting and chewing steps should be repeated periodically. For example, the balancing procedure may be performed every 6-24 months.

By utilizing the present method of intraoral occlusal adjustment and balancing the bite of the patient, stresses that were previously concentrated in the area of the high spots are evenly distributed across the natural teeth/restoration, This even distribution of stress during chewing extends the life of the gum and bone supporting the teeth/restoration. Accordingly, the dental health of the patient is significantly enhanced and expensive procedures to repair certain gum diseases and rebuild periodontal bone may often be avoided.

Further, these advantages are achieved without placing the patient at a significant health risk. More specifically, the method is only performed under the supervision of a trained dental professional. To insure this, the abrasive containing chewing compound may only be sold to the dental professional not over-the-counter. Further, the method is only performed in the dental office and the chewing compound is never taken home by the patient.

Additionally, the method is not utilized where certain patient conditions exist. Contraindications include but are not limited to (a) recent placement of restorations (e.g. within the last twelve hours), (b) a patient under the influence of anaesthesia, (c) a patient suffering from any acute or chronic soft tissue infection and (d) a patient suffering from any open lesion.

In summary, numerous benefits result from applying the concepts of the present invention. More particularly, the natural chewing action of the patient is utilized to balance the bite. Accordingly, the natural occlusal plane is preserved and the teeth/restoration are brought into the best possible mesh. The problem of over balancing and the destroying of good tooth structure prevalent when utilizing the prior art procedure of removing high spots with a grinding tool are advantageously avoided. Further, it should be appreciated that the present procedure is safe, simple and inexpensive. It may also be conveniently completed within approximately 15–30 minutes during a normal visit to the general dentistry practitioner for a checkup.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

I claim:

1. A method of providing better occlusion between natural teeth of the upper and lower Jaw bones, comprising the steps of:
   examining the occlusion of the natural teeth and identifying high spots;
   grinding down particularly prominent high spots;
   selecting a non-tacky and abhesive chewing compound that does not stick to natural teeth but holds an abrasive of a grade of between 100–220 grit for providing controlled abrasive action on said natural teeth during chewing;
   chewing said chewing compound that holds the abrasive for a period of 3–15 minutes to abrade high spots and provide overall better occlusion.

2. The method set forth in claim 1 including reexamining the occlusion of the natural teeth following chewing of said abrasive chewing material.

3. The method set forth in claim 2, including selecting a chewing compound including an abrasive of a grade between 100 and 200 grit, for providing controlled abrasive action on said natural teeth and chewing said abrasive chewing compound for a period of from three to fifteen minutes all following said reexamination.

4. The method set forth in claim 3, including sitting upright prior to chewing and expelling abrasive released from said chewing compound during said chewing.

5. The method set forth in claim 4, including selecting a chewing compound including a polish for said natural teeth and chewing said polishing chewing compound for a period of time of from three to fifteen minutes all following said reexamination.

6. The method set forth in claim 5, including sitting upright prior to chewing and expelling polish released from said chewing compound during said chewing.

7. The method set forth in claim 5, including rinsing with an antiseptic following chewing of said polishing chewing material.

8. The method set forth in claim 1, including sitting upright prior to chewing and expelling abrasive released from said chewing compound during said chewing.

9. The method set forth in claim 1, including rinsing with an antiseptic following chewing of said abrasive chewing material.

10. The method set forth in claim 1, including repeating said examining, selecting and chewing steps as necessary to maintain proper occlusion between said natural teeth of the upper and lower jaw bones.

11. The method set forth in claim 10, wherein said examining, selecting and chewing steps are repeated every six to twenty-four months.

12. A method for providing better occlusion between a dental restoration and natural teeth of a patient comprising the steps of:
    positioning the dental restoration in the month of a patient;
    examining the occlusion of the dental restoration and natural teeth and identifying high spots;
    grinding down particularly prominent high spots;
    selecting a non-tacky and abhesive chewing compound that does not stick to natural teeth and dental restorations but holds an abrasive of a grade between 100–220 grit for providing controlled abrasive action on said dental restoration and natural teeth;
    chewing said chewing compound that holds the abrasive for a period of 3–15 minutes to abrade high spots and provide overall better occlusion.

13. The method set forth in claim 12, including reexamining the occlusion of the dental restoration and natural teeth following chewing of said abrasive chewing material.

14. The method set forth in claim 13, including repeating said selecting and chewing steps set forth in claim 12 following said reexamining step.

15. The method set forth in claim 14, including sitting upright prior to chewing and expelling abrasive released from said chewing compound during said chewing.

16. The method set forth in claim 13, including selecting a non-stick chewing compound including a polish for said natural teeth and chewing said polishing chewing compound for a period of time from three to fifteen minutes all following said reexamination.

17. The method set forth in claim 16, including sitting upright prior to chewing and expelling polish released from said chewing compound during said chewing.

18. The method set forth in claim 17, including rinsing with an antiseptic following chewing.

19. The method set forth in claim 12, including sitting upright prior to chewing and expelling abrasive released from said chewing compound during said chewing.

20. The method set forth in claim 12, including repeating said examining, selecting and chewing steps as necessary to maintain proper occlusion between said dental restoration and said natural teeth.

21. A method for providing better occlusion of a complete dental restoration including both upper and lower plates of a patient comprising:
    positioning the upper and lower plates in the mouth of said patient;
    examining the occlusion of the upper and lower plates;
    grinding down particularly prominent high spots;
    selecting a non-tacky and abhesive chewing compound that does not stick to dental restorations but holds an abrasive of a grade of between 100–220 grit for providing controlled abrasive action on said upper and lower plates;
    chewing said chewing compound that holds the abrasive for a period of time between 3–15 minutes to abrade upper and lower plates and provide overall better occlusion.

22. The method set forth in claim 21, including reexamining the occlusion of said upper and lower plates following chewing of said abrasive chewing material.

23. The method set forth in claim 22, including repeating said selecting and chewing steps set forth in claim 21 following said reexamining step.

24. The method set forth in claim 22, including selecting a non-stick chewing compound including a polish for said upper and lower plate and chewing said polishing chewing compound for a period of time from three to fifteen minutes all following said reexamination.

25. The method set forth in claim 22, including sitting upright prior to chewing and expelling polish released from said chewing compound during said chewing.

26. The method set forth in claim 22, including rinsing with an antiseptic following chewing.

27. The method set forth in claim 21, including sitting upright prior to chewing and expelling abrasive released from said chewing compound during said chewing.

28. The method set forth in claim 21, including rinsing with an antiseptic following chewing.

29. The method set forth in claim 21, including repeating said examining, selecting and chewing steps as necessary to maintain proper occlusion between said upper and lower plates of said dental restoration.

* * * * *

UNITED STATES PATENT AND TRADEMARK OFFICE
CERTIFICATE OF CORRECTION

PATENT NO. : 5,423,681
DATED : Jun. 13, 1995
INVENTOR(S) : James L. Rose

It is certified that error appears in the above-indentified patent and that said Letters Patent is hereby corrected as shown below:

In Claim 12, column 8, line 7, change "month" to --mouth--.

Signed and Sealed this

Twenty-sixth Day of March, 1996

Attest:

BRUCE LEHMAN

*Attesting Officer*  *Commissioner of Patents and Trademarks*